(12) United States Patent
Geist et al.

(10) Patent No.: US 10,092,730 B2
(45) Date of Patent: Oct. 9, 2018

(54) COMPOSITE WIRES FOR USE IN MEDICAL PROCEDURES AND ASSOCIATED METHODS

(71) Applicant: Summit Access, LLC, Parker, CO (US)

(72) Inventors: Leroy D. Geist, Aurora, CO (US); LeRoy D. Jutte, Highlands Ranch, CO (US)

(73) Assignee: Summit Access, LLC, Englewood, CO (US)

( * ) Notice: Subject to any disclaimer, the term of this patent is extended or adjusted under 35 U.S.C. 154(b) by 520 days.

(21) Appl. No.: 14/147,352

(22) Filed: Jan. 3, 2014

(65) Prior Publication Data
US 2014/0188082 A1    Jul. 3, 2014

Related U.S. Application Data

(60) Provisional application No. 61/748,699, filed on Jan. 3, 2013.

(51) Int. Cl.
*A61M 25/09*    (2006.01)
*A61M 25/00*    (2006.01)

(52) U.S. Cl.
CPC ........ *A61M 25/09* (2013.01); *A61M 25/0009* (2013.01); *A61M 2025/09108* (2013.01);
(Continued)

(58) Field of Classification Search
CPC .............. A61B 17/8897; A61M 25/09; A61M 2025/018; A61M 2025/0175;
(Continued)

(56) References Cited

U.S. PATENT DOCUMENTS 5,300,032 A * 4/1994 Hibbs ............... A61M 25/0069
604/164.1
5,772,609 A * 6/1998 Nguyen ................ A61M 25/09
600/585
(Continued)

FOREIGN PATENT DOCUMENTS

DE     102007005559 B4    7/2008
EP        0820782 A3      1/1998
(Continued)

OTHER PUBLICATIONS

United States Patent and Trademark Office Acting as the International Search Authority, "International Search Report and Written Opinion," dated May 7, 2014, in related PCT application No. PCT/US2014/010217.
(Continued)

*Primary Examiner* — Nathan R Price
*Assistant Examiner* — Gerald Landry, II
(74) *Attorney, Agent, or Firm* — Durham Jones & Pinegar, P.C., Intellectual Property Law Group

(57) ABSTRACT

A composite wire, such as a guide wire, may include a principal section with a relatively large outer diameter, as well as one or more reduced sections with smaller outer diameters. The relatively small outer diameter of each reduced section may be defined by an inner element of the composite wire, while the relatively large outer diameter of the principal section may be defined by one or more outer elements that reside on, and may surround, the inner element. The inner and outer elements may be formed from materials that impart the composite wire with one or more desired characteristics, such as a stiffness, hardness and flexibility. In specific embodiments, the inner element may comprise a standard, small diameter guide wire, while the outer element comprises a tube formed from polyether ether ketone (PEEK). Each outer element may be secured to the
(Continued)

inner element at one or more locations. Differences in characteristics between locations where the outer element has been coupled to the inner element and locations where the outer element merely resides on the inner element may be used to tailor characteristics of the composite wire.

25 Claims, 2 Drawing Sheets

(52) U.S. Cl.
CPC .............. *A61M 2025/09133* (2013.01); *Y10T 29/49826* (2015.01)

(58) Field of Classification Search
CPC ........... A61M 2025/09125; A61M 2025/0063; A61M 25/0102
USPC ................. 604/95.04, 164.13, 510, 523, 528
See application file for complete search history.

(56) References Cited

U.S. PATENT DOCUMENTS

| | | | | |
|---|---|---|---|---|
| 5,792,144 A * | 8/1998 | Fischell | ................. | A61F 2/958 606/108 |
| 5,827,201 A * | 10/1998 | Samson | ................ | A61M 25/09 600/585 |
| 6,004,279 A * | 12/1999 | Crowley | ............... | A61M 25/09 600/433 |
| 6,106,486 A * | 8/2000 | Tenerz | ................ | A61B 5/6851 600/585 |
| 6,329,069 B1 * | 12/2001 | Azizi | .................... | B21C 37/042 428/600 |
| 6,340,441 B1 * | 1/2002 | Meyer | ................... | A61M 25/09 156/244.12 |
| 6,488,637 B1 * | 12/2002 | Eder | .................... | A61L 31/022 600/585 |
| 6,547,766 B1 * | 4/2003 | Fitz | .................. | A61M 25/0023 604/264 |
| 7,883,474 B1 * | 2/2011 | Mirigian | ............... | A61M 25/09 600/585 |
| 8,083,690 B2 * | 12/2011 | Peterson | ............... | A61M 25/09 600/585 |
| 9,498,603 B2 * | 11/2016 | Parodi | ................... | A61M 25/09 |
| 2004/0167439 A1 * | 8/2004 | Sharrow | .............. | A61M 25/09 600/585 |
| 2004/0167441 A1 * | 8/2004 | Reynolds | .............. | A61L 31/022 600/585 |
| 2005/0016755 A1 * | 1/2005 | Martinez | ................ | H01B 3/441 174/120 R |
| 2005/0124917 A1 * | 6/2005 | Skujins | ................. | A61M 25/09 600/585 |
| 2006/0198976 A1 * | 9/2006 | Trapp | ..................... | A61L 29/04 428/36.9 |
| 2007/0299366 A1 * | 12/2007 | Sharrow | .............. | A61M 25/09 600/585 |
| 2008/0119869 A1 * | 5/2008 | Teague | ................. | A61B 17/221 606/127 |
| 2008/0154152 A1 * | 6/2008 | Satou | .................... | A61M 25/09 600/585 |
| 2008/0194991 A1 * | 8/2008 | Teague | ................. | A61M 25/09 600/585 |
| 2008/0262430 A1 * | 10/2008 | Anderson | .......... | A61B 17/3415 604/164.1 |
| 2008/0281228 A1 * | 11/2008 | Parodi | ................... | A61M 25/09 600/585 |
| 2009/0143768 A1 * | 6/2009 | Parodi | ................... | A61M 25/09 604/528 |
| 2009/0163818 A1 | 6/2009 | Zelenka et al. | | |
| 2010/0318064 A1 | 12/2010 | Derrick et al. | | |
| 2011/0015617 A1 | 1/2011 | Chesnin et al. | | |
| 2012/0078232 A1 * | 3/2012 | Schulting | .......... | A61M 25/0068 604/528 |
| 2013/0226033 A1 * | 8/2013 | Eskuri | ................... | A61M 25/09 600/585 |

FOREIGN PATENT DOCUMENTS

| | | |
|---|---|---|
| EP | 0994742 B1 | 9/2004 |
| JP | 2006057159 A | 3/2006 |

OTHER PUBLICATIONS

Japanese Patent Office, "Notice of Reasons for Rejection" dated Jul. 25, 2016, in Japanese patent application No. 2015-551785.

European Patent Office, "Supplementary European Search Report" dated Sep. 6, 2016, in European patent application No. 14735135.7.

First Office Action dated Feb. 28, 2017 received from State Intellectual Property Office of the People's Republic of China for Application No. 201480007844.7.

Second Office Action dated Sep. 22, 2017 received from State Intellectual Property Office of the People's Republic of China for Application No. 201480007844.7.

* cited by examiner

COMPOSITE WIRES FOR USE IN MEDICAL PROCEDURES AND ASSOCIATED METHODS

CROSS-REFERENCE TO RELATED APPLICATION

A claim for priority under 35 U.S.C. § 119(e) is hereby made to U.S. Provisional Patent Application No. 61/748,699, filed on Jan. 3, 2013, titled "COMPOSITE WIRES FOR USE IN MEDICAL PROCEDURES AND ASSOCIATED METHODS," the entire disclosure of which is, by this reference, hereby incorporated herein.

TECHNICAL FIELD

This disclosure relates generally to wires for use in medical procedures (e.g., guide wires, stylets, etc.) and, more specifically, to wires that have a relatively large outer diameter along at least a portion of their lengths and taper down to a relatively small outer diameter at an end portion. Even more specifically, this disclosure relates to composite wires in which at least one outer element defines the relatively large outer diameter and an inner element defines the relatively small outer diameter.

RELATED ART

U.S. Pat. No. 8,083,690 to Peterson et al. discloses a guide wire converter that increases the length of a guide wire. The guide wire extender includes a tubular end that is configured to fit over and to be secured to a reduced-diameter end section of a guide wire, effectively extending the length of the guide wire. Since the guide wire includes a section with a reduced outer diameter, the guide wire must be machined during its manufacture. Machining or other types of additional processing may undesirably increase the complexity and cost of the manufacturing process and, thus, the cost of the finished product.

SUMMARY

A wire with a composite structure, which is also referred to herein as a composite wire, may include an inner element and at least one outer element. The inner element may be longer than the outer element, providing the wire with at least one section of effectively reduced diameter. In some embodiments, a transition from the section of effectively reduced diameter to the largest outer diameter of the outer element may include a taper.

The inner element comprises an elongate element, such as a wire (e.g., a guide wire, etc.), that may define a length of the composite wire. The inner element has a relatively small outer diameter, or "first outer diameter," that may define the outer diameter of at least one section of the length of the tapered wire. The outer diameter of the inner element (and, thus, the outer cross-sectional shape of the inner element) may be uniform or substantially uniform (accounting for any tolerance required by manufacturing processes) along the entire length of the inner element. In a specific embodiment, the inner element may comprise a small diameter (e.g., 0.018 inch, 0.014 inch, etc.) guide wire.

Each outer element may comprise an elongate, tubular structure. A lumen that extends through at least a portion of each outer element may have an inner diameter that corresponds to (e.g., is slightly larger than, is the same size as, is slightly smaller than, etc.) an outer diameter of each portion of the inner element over which the outer element is configured to be placed. The outer element may have a relatively large outer diameter, or a "second outer diameter," that is uniform or substantially uniform along substantially an entire length of the outer element. In some embodiments, the outer surface of an outer element that has a uniform or substantially uniform outer diameter along substantially its entire length may include taper from the relatively large outer diameter to a smaller dimension (e.g., the relatively small outer diameter, an outer diameter slightly larger than the relatively small outer diameter, etc.) at or near at least one end of the outer element. In other embodiments, at least a portion of the transition provided by the outer element from the relatively large outer diameter to the relatively small outer diameter may be stepped. The outer element may be formed from a material that has properties (e.g., stiffness, flexibility, hardness, etc.) that are similar to the properties of the inner element. As a non-limiting example, the outer element may comprise a relatively hard, yet flexible polymer, such as polyether ether ketone (PEEK).

Each outer element of a composite catheter may be secured to the inner element in a manner that prevents the outer element from moving (e.g., sliding, etc.) longitudinally along the inner element. In some embodiments, one or more portions of each outer element may be adhered to the inner element. Adhesion may be facilitated by way of an adhesive material between the inner element and the outer element. The adhesive material may comprise a curable adhesive.

Regions of a composite wire that include hardened or cured adhesive may differ in stiffness and/or flexibility from sections of the composite wire that lack hardened or cured adhesive. Accordingly, the stiffness and/or flexibility of various sections of a composite wire may be tailored in a desired manner. As a non-limiting example, a composite wire include a proximal end that is stiffer and less flexible than a majority of the remainder of the length of the composite wire, including a distal section of the composite wire.

In a method for manufacturing a composite wire, a series of outer elements may be extruded with periodic sections of reduced diameter. In some embodiments, each end of each section of reduced diameter may taper from the relatively large outer diameter to the relatively small outer diameter. This elongate extrusion may be divided (e.g., cut, etc.) into a plurality of individual outer elements by separating it at the center of each section of reduced diameter and at the center of each relatively large outer diameter section. Each outer element may then be assembled with an inner element. Assembly may include placement of an adhesive material between at least a portion of the outer element and a corresponding portion of the inner element. In embodiments where the wire includes an adhesive material, the adhesive material may be placed within the lumen of the outer element prior to introducing the inner element into the lumen. Alternatively, the adhesive material may be introduced between the outer element and the inner element (e.g., at one or both ends of each outer element, etc.) after they have been assembled with one another. In some embodiments, the adhesive material may be cured. When the foregoing or similar process elements are used to define a composite wire, the composite wire may be imparted with two or more different outer dimensions at two or more locations without requiring that any portion of the wire be machined.

Other aspects, as well as features and advantages of various aspects, of the disclosed subject matter will become apparent to those of ordinary skill in the art through consideration of the ensuing description, the accompanying drawings and the appended claims.

DETAILED DESCRIPTION

Figure 1:
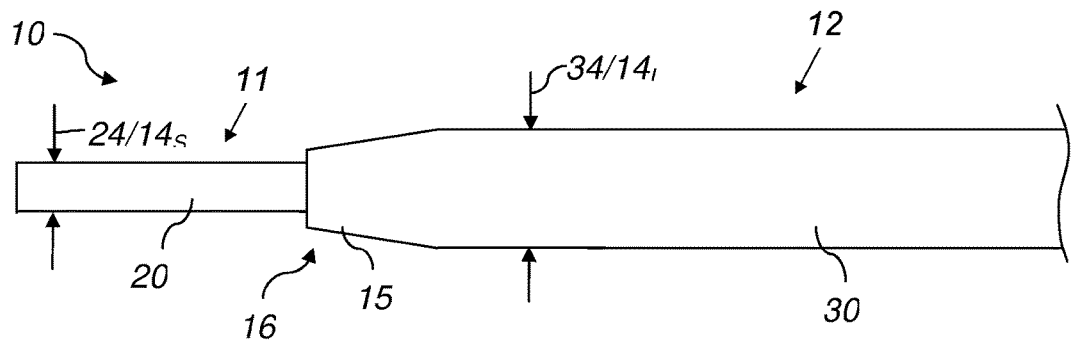
FIG. 1 depicts an embodiment of composite wire that tapers from a relatively small outer diameter at and near a distal end of the composite wire to a relatively large outer diameter at a more proximal location along the length of the composite wire.
Figure 2:
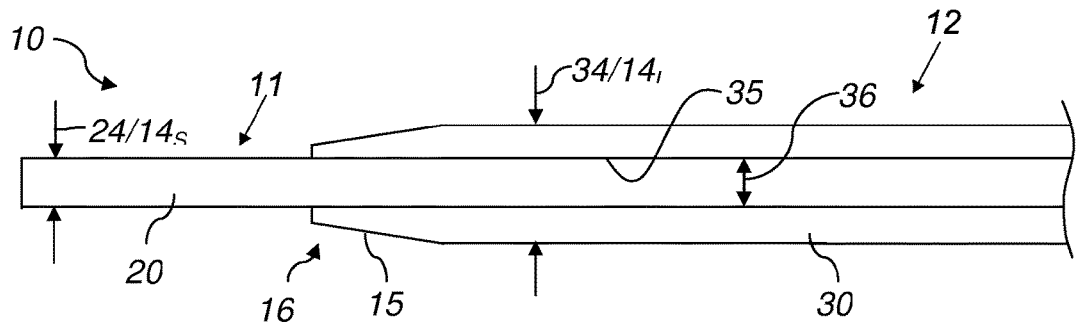
FIG. 2 illustrates a cross-section through the length of the embodiment of composite wire shown in FIG. 1.

FIGS. 1 and 2 depict an embodiment of a composite wire 10. The composite wire 10 includes at least one reduced section 11, which may have a relatively small outer diameter, and at least one main section 12, which has a relatively large outer diameter. The composite wire 10 includes an inner element 20 and an outer element 30. The inner element 20 may define the reduced section 11 of the composite wire 10. The outer element 30 resides on at least a portion of the inner element 20, and may define the at least one main section 12. One or more coupling elements 40 (FIG. 4) may secure the outer element 30 in place on the inner element 20 of the composite wire 10.

The inner element 20 may comprise a wire, such as a guide wire, a stylet or the like of known configuration. Thus, the inner element 20 may be elongated. In some embodiments, a length of the inner element 20 may define a length of the composite wire 10. A few examples of lengths include, but are not limited to, 45 cm, 80 cm, 125 cm, 145 cm, 150 cm, 180 cm and 260 cm. The inner element 20 may be formed from any suitable material, such as a single filament of a suitable metal or metal alloy (e.g., stainless steel, NiTiNOL, etc.), a central filament of a suitable metal or metal alloy wrapped with a coil formed from another suitable metal or metal alloy. Alternatively, polymeric configurations of wires, including reinforced polymers (e.g., glass fiber filled, carbon fiber filled, etc.), may be used as the inner element 20 of a composite wire 10. As another alternative, the inner element 20 may include a combination of metal/metal alloy and polymer elements.

In addition, the inner element 20 may have an outer diameter 24 that is uniform or substantially uniform, accounting for tolerances in the process of manufacturing the inner element 20 (e.g., guide wire manufacturing processes, stylet manufacturing processes, etc.), along an entirety of the length or substantially the entirety of the length, of the inner element 20. The outer diameter 24 of the inner element 20 may define a relatively small outer diameter $14_S$, or a first outer diameter, of the composite wire 10. Specific embodiments of inner elements 20 have outer diameter 24 of 0.010 inch to 0.018 inch (e.g., 0.010 inch, 0.014 inch, 0.018 inch, etc.) or any other suitable outer diameter.

Figure 2A:
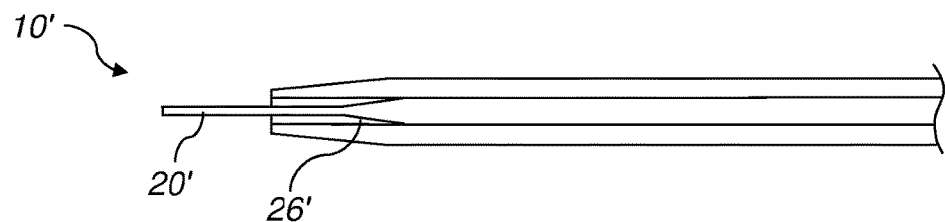
FIGS. 2A through 2C are partial cross-sectional representations of other embodiments of composite wires.
Figure 2B:
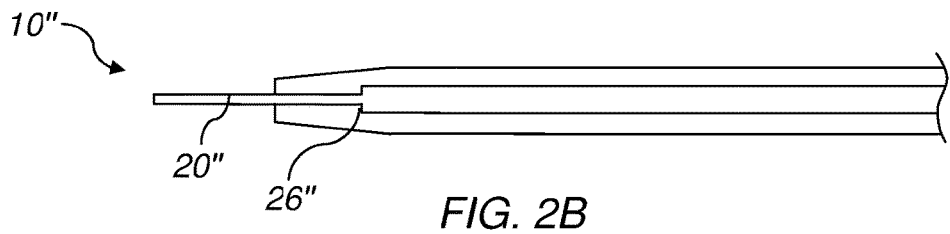

As an alternative to an inner element 20 with a uniform outer diameter, various embodiments of composite wires 10', 10", 10'" may include inner elements 20', 20", 20'" that have non-uniform outer diameters. The embodiment of composite wire 10' shown in FIG. 2A includes an inner element 20' with at least one taper 26'. FIG. 2B shows an embodiment of composite wire 10" that includes an inner element 20" with a stepped transition 26" from a section with a relatively large outer diameter to a section with a smaller outer diameter. In other embodiments, the inner element 20'" of a composite wire 10" may have a substantially uniform outer diameter 22'" interrupted by one or more recesses 23'" (e.g., circumferential grooves, etc.).

The outer element 30 of a composite wire 10 may comprise a tubular structure. Accordingly, the outer element 30 may include a lumen 35 that extends through all or part of its length. The lumen 35 of the outer element 30 may have an inner diameter 36 that enables the lumen 35 to receive at least a portion of the inner element 20. The inner diameter 36 of the lumen 35 may be slightly larger than the outer diameter 24 of the inner element 20. For example, an outer element 30 may include a lumen 35 with an inner diameter 36 of about 0.015 inch to receive an inner element 20 that has an outer diameter 24 of 0.014 inch. As another example, an outer element 30 with a lumen 35 that has an inner diameter 36 of 0.019 inch may be configured to receive an inner element 20 with an outer diameter 24 of 0.018 inch. Alternatively, the inner diameter 36 of the lumen 35 of an outer element 30 may be about the same as, or even slightly smaller than, the outer diameter 24 of the inner element 20. The outer element 30 may have a configuration (e.g., a structure, a material, etc.) that enables such a lumen 35 to at least temporarily expand to receive the inner element 20.

An outer diameter 34 of the outer element 30 may be configured to impart the main section 12 of the composite wire 10 with a desired outer diameter. Without limitation, examples of principal outer diameters for a composite wire include 0.025 inch to 0.040 inch (e.g., 0.025 inch, 0.035 inch, 0.038 inch, etc.).

In some embodiments, including embodiments in which the lumen 35 of the outer element 30 extends through the entire length of the outer element 30, the outer element 30 may be configured to completely reside on the inner element 20. Such an outer element 30 may have a length that is only slightly shorter than a length of the inner element 20 of the composite wire 10. Without limitation, the length of the outer element 30 may be about one centimeter (1 cm) to about twenty-five centimeters (25 cm) shorter than the length of the inner element 20. These relative configurations may provide for a composite wire 10 with an end (e.g., a distal end, etc.) with a relatively small diameter $14_S$ and a length 19 that is substantially the same as the difference between the length of the inner element 20 and the length of the outer element 30 (e.g., about 1 cm to about 25 cm, etc.).

In other embodiments, the length of each outer element 30 may be substantially shorter than the length of the inner element 20 of a composite wire 10. When relatively short outer elements 30 are used with relatively long inner elements 20, more than one outer element 30 may be assembled with an inner element 20. In embodiments where a composite wire 10 includes two or more outer elements 30, and the outer elements 30 are spaced apart from one another along the length of the inner element 20 (e.g., the inner element 20 is exposed between adjacent outer elements 30, the composite wire may include at least one medially located region with a relatively small outer diameter. Of course, such an embodiment may also include a distal portion and/or a proximal portion with the relatively small outer diameter.

The outer element 30 of a composite wire 10 may be formed from a material that, along with the configuration of the outer element 30, imparts the composite wire 10 with one or more desired characteristics, such as stiffness, flexibility, hardness, or the like. In addition, the material(s) from which the outer element 30 is formed may be appropriate for the intended use of the composite wire 10 (e.g., compatible for use in medical processes, such as catheterization, etc.). In some embodiments, the outer element 30 and its material may be selected to maintain or substantially maintain one or more characteristics (e.g., stiffness, flexibility, hardness, etc.) of the inner element 20 of the composite wire 10. In other embodiments, the outer element 30 and/or its material may be selected to modify one or more characteristics (e.g., increase stiffness, decrease flexibility, change the hardness, etc.) of the inner element 20. The outer element 30, when positioned over an inner element 20 that comprises a standard guide wire, may be configured to define a composite wire 10 with characteristics that are the same as or comparable to a standard guide wire that has the same outer diameter.

A non-limiting example of a material from which the outer element 30 may be formed is a relatively hard, yet flexible polymer. Additionally, the material from which the outer element 30 is formed may transmit (e.g., be transparent or translucent to) ultraviolet (UV) radiation. A specific embodiment of a polymer that may be used to form the outer element 30 is polyether ether ketone (PEEK). Of course, other polymers with desired characteristics may be used to form the outer element 30 as well.

As illustrated by FIGS. 1 and 2, at least one transition 15 between the relatively large outer diameter $14_L$ and the relatively small outer diameter $14_S$ of a composite wire 10 may include a taper 16. In the depicted embodiment, the taper 16 is located near a distal end of the composite wire 10.

Figure 3:
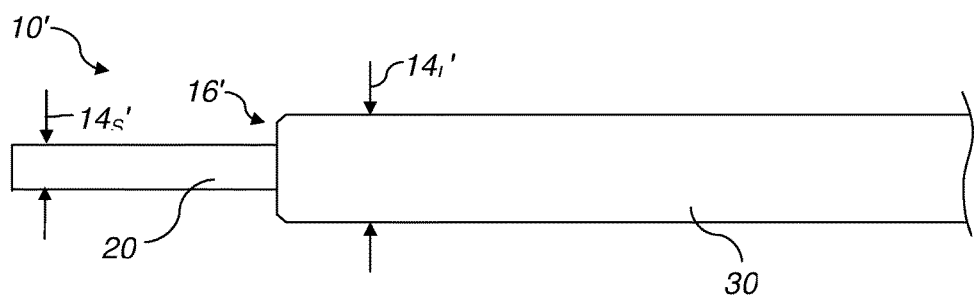
FIG. 3 shows another embodiment of composite wire, in which a transition from a relatively small outer diameter section to a relatively large outer diameter section.

Alternatively, as illustrated by FIG. 3, a transition 16' from a section of composite wire 10'''' that has a relatively large outer diameter $14_L$ and an adjacent section with a relatively small outer diameter $14_S$ may be less gradual. More specifically, the transition 16' may be stepped.

Figure 4:
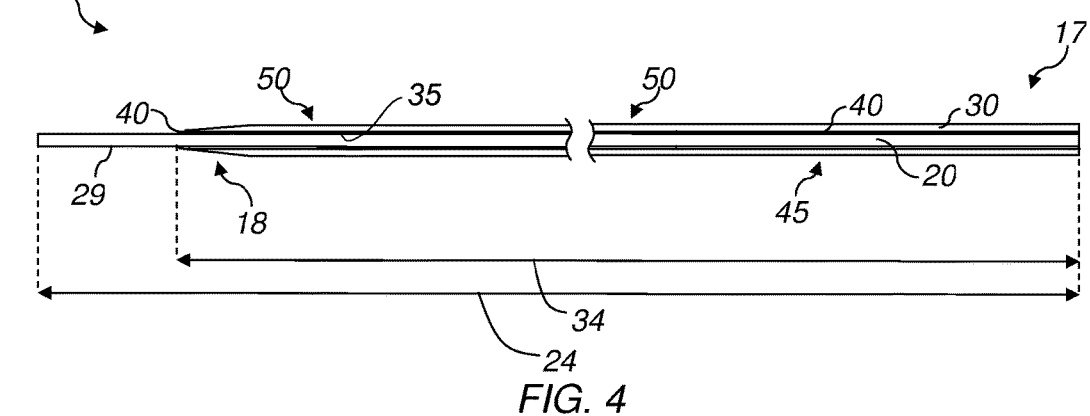
FIG. 4 depicts an embodiment of composite wire with sections of different stiffnesses and flexibilities.

Turning now to FIG. 4, once an outer element 30 has been assembled with an inner element 20 and positioned at a desired location along the length of the inner element 20, the outer element 30 may be secured to the inner element 20. In some embodiments, one or more relatively small portions (e.g., short annular portions, longer sections, etc.) of the outer element 30 may be secured to the inner element 20. In other embodiments, much longer sections of the outer element 30 (e.g., an entire length of the outer element 30, substantially an entire length of the outer element 30, etc.) may be secured to the inner element 20.

Figure 2C:
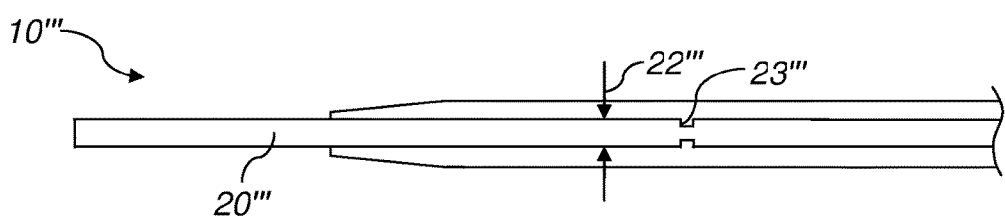

Any suitable technique may be used to secure the outer element 30 to the inner element 20. In some embodiments, a composite wire 10 may include one or more relatively short coupling elements 40 that secure the outer element 30 to the inner element 20. The coupling element 40 may be in the form of a spot, ring or band, or it may have any other suitable configuration. A coupling element 40 may be located at least partially within the lumen 35 of the inner element 20, between the inner element 20 and the outer element 30. As another option, a coupling element 40 may be located between an end of the outer element 30 and an outer surface 29 of the inner element 20. Alternatively, a coupling element 40 may be configured to extend a greater distance along the lengths of the inner element 20 and the outer element 30 and, in some embodiments, the coupling element 40 may extend along substantially the entire length of the outer element 30. With added reference to FIGS. 2A through 2C, a coupling element 40 may reside in a gap (e.g., a region of reduced diameter, a recess, etc.) between the inner element 20 and a surface of the lumen 35 through the outer element 30.

In some embodiments, each coupling element 40 may comprise a cured adhesive material. In some embodiments, the cured adhesive material may comprise a UV-curable adhesive material. Alternatively, the adhesive material may comprise a two-part (i.e., catalyst curable) epoxy, a heat curable epoxy, or any other suitable adhesive material.

As an alternative to using adhesive coupling elements 40, the outer element 30 may be mechanically, but non-adhesively secured to the inner element 20 at one or more locations. Without limitation, in embodiments where the outer element 30 contracts, or shrinks, when exposed to heat and remains contracted when the heat is removed, the one or more locations of the outer element 30 may be caused to grasp or otherwise engage the inner element 20. In some embodiments, an entire length of each outer element 30 may mechanically engage the inner element 20.

Referring now to FIG. 4, the coupled locations 45 of a composite wire 10, where the outer element 30 is secured to the inner element 20, may have different characteristics (e.g., stiffness, flexibility, hardness, etc.) than uncoupled locations 50 of the composite wire 10, where the outer element 30 merely resides on the inner element 20. The differences in characteristics between the coupled locations 45 and the uncoupled locations 50 may be attributable to any of a number of different factors. As an example, the inability of the inner element 20 and outer element 30 to move longitudinally, or slide, relative to one another at a coupled location 45 may make the coupled location 45 stiffer and less flexible than an uncoupled location 50, where the inner element 20 and the outer element 30 can move longitudinally relative to one another. As another example, a physical property of a coupling element 40 (e.g., an adhesive material, etc.) may increase the stiffness and hardness of a coupled location 45 relative to each uncoupled location 50, while decreasing the flexibility of the coupled location 45. The different characteristics between the coupled location(s) 45 of a composite wire 10 and the uncoupled location(s) 50 of the composite wire 10 may be exploited in a way that enables tailoring of the composite wire 10 to include sections with different, desired properties. By way of example, and without limitation, a composite wire 10 may include a relatively stiff proximal end 17, which may facilitate handling or manipulation of the composite wire 10, and a more flexible distal end 18, which may minimize any risk of trauma that may be caused as the composite wire 10 is introduced into or moved through the body of a subject.

With returned reference to FIGS. 1 and 2, an embodiment of a method for manufacturing a composite wire 10 will now be described. A series of outer elements 30 may be formed by known processes. In a specific embodiment, the series of outer elements 30 may be formed by extruding material through a die. The material may be extruded in a manner that enables the formation of relatively long sections with a constant or substantially constant outer diameter that are periodically interrupted by short sections that transition (e.g., taper, step, etc.) from the outer diameter of the long sections to a smaller outer diameters, then transition back to the larger outer diameter of the long sections. These interruptions, or necked down regions, may be formed by altering the rate at which the extruded material is pulled from the extrusion die, with each long section being pulled at a constant rate, and each necked down region being pulled at a faster rate. Once an elongate element with a plurality of long sections has been formed, it may be divided (e.g., cut, etc.) into a plurality of individual outer elements 30 by separating the elongate element at the center of each necked down region and separating each long section into two separate pieces. Each outer element 30 made by such a process (or by any other suitable process) may then be assembled with an inner element 20. Assembly may include placement of an adhesive material between at least a portion of the outer element 30 and a corresponding portion of the inner element 20. In embodiments where the composite wire 10 includes an adhesive material, the adhesive material may be placed within the lumen 35 of the outer element 30, on the inner element 20, or in recesses in or recessed areas of the surface of the inner element 20. Alternatively, the adhesive material may be introduced between the outer element 30 and the inner element 20 (e.g., at one or both ends of each outer element, etc.) after they have been assembled with one another. In some embodiments, the adhesive material may be cured. In any event, the adhesive material forms one or more coupling elements 40 between the inner element 20 and the outer element 30.

Although the foregoing description includes many specifics, these should not be construed as limiting the scope of the invention recited by any of the appended claims, but merely as providing information pertinent to some specific embodiments that may fall within the scope of one or more of the appended claims. Features from different embodiments may be employed in combination. In addition, other embodiments may also lie within the scope of one or more of the appended claims. All additions to, deletions from and modifications of the disclosed subject matter that fall within the scope of any of the appended claims are to be embraced by that claim.

What is claimed:

1. A composite wire for use in a medical procedure, comprising:
   an inner element comprising an elongated structure having a first outer diameter and a first length, the first outer diameter of the inner element being uniform along an entirety of the first length of the inner element;
   an outer element comprising an elongated structure comprising a polymer and having a second outer diameter and a second length, and including a lumen extending through an entirety of the second length, the lumen having an inner diameter receiving the first outer diameter of the inner element, the inner diameter of the outer element being about the same as the first outer diameter of the inner element, the second length being shorter than the first length; and
   adhesive material between the inner element and the outer element, the adhesive material securing the inner element within the outer element,
   the inner element and the outer element having an assembled relationship in which:
      the outer element is secured by the adhesive material to the inner element to prevent movement of the outer element along a length of the inner element;
      at least a portion of the inner element is exposed laterally beyond an end of the outer element to form at least one reduced section of a composite wire; and
      the outer element forms at least one principal section of the composite wire.

2. The composite wire of claim 1, wherein the inner element comprises a guide wire.

3. The composite wire of claim 2, wherein the outer diameter of the guide wire is 0.010 inch to 0.018 inch.

4. The composite wire of claim 2, wherein the guide wire comprises a standard guide wire that comprises a metal, a metal alloy or a polymer.

5. The composite wire of claim 1, wherein an outer diameter of the inner element defines an outer diameter of the reduced section of the composite wire.

6. The composite wire of claim 1, wherein the outer element comprises polyether ether ketone (PEEK).

7. The composite wire of claim 1, wherein the second outer diameter is 0.025 inch to 0.040 inch.

8. The composite wire of claim 1, wherein the second outer diameter defines a principal outer diameter of the composite wire.

9. The composite wire of claim 1, including a tapered region at an end of the outer element.

10. The composite wire of claim 1, wherein the adhesive material comprises a UV-curable adhesive.

11. A composite wire for use in a medical procedure, comprising:
    an inner element comprising an elongated structure having a first outer diameter and a first length;
    an outer element comprising an elongated structure comprising a polymer and having a second outer diameter and a second length, and including a lumen extending through an entirety of the second length, the lumen having an inner diameter receiving the first outer diameter of the inner element, the inner diameter of the outer element being about the same as the first outer diameter of the inner element, the second length being shorter than the first length; and
    adhesive between the inner element and the outer element securing the inner element within the outer element,
    the inner element and the outer element having an assembled relationship in which:
       the outer element is secured to the inner element to prevent movement of the outer element along a length of the inner element;
       at least a portion of the inner element is exposed laterally beyond an end of the outer element to form at least one reduced section of a composite wire, an outer diameter of the inner element defining an outer diameter of the at least one reduced section of the composite wire; and
       the outer element forms at least one principal section of the composite wire.

12. The composite wire of claim 11, wherein the inner element has a non-uniform outer diameter.

13. The composite wire of claim 11, wherein at least one recess is formed in an outer surface of the inner element.

14. The composite wire of claim 11, wherein the inner element comprises a guide wire.

15. The composite wire of claim 11, wherein the second outer diameter defines a principal outer diameter of the composite wire.

16. The composite wire of claim 11, including a tapered region at an end of the outer element.

17. The composite wire of claim 11, wherein the adhesive comprises a coupling element between the inner element and the outer element.

18. The composite wire of claim 17, wherein the adhesive comprises a UV-curable adhesive.

19. A composite wire for use in a medical procedure, comprising:
    an inner element comprising an elongated structure having a first outer diameter and a first length;
    an outer element comprising an elongated structure comprising a polymer and having a second outer diameter and a second length, and including a lumen extending through an entirety of the second length, the lumen having an inner diameter receiving the first outer diameter of the inner element, the inner diameter of the outer element being about the same as the first outer diameter of the inner element, the second length being shorter than the first length;

a tapered region at an end of the outer element; and adhesive between the inner element and the outer element securing the inner element within the outer element, the inner element and the outer element having an assembled relationship in which:

the outer element is secured to the inner element to prevent movement of the outer element along a length of the inner element;

at least a portion of the inner element is exposed laterally beyond an end of the outer element to form at least one reduced section of a composite wire; and the outer element forms at least one principal section of the composite wire.

20. The composite wire of claim 19, wherein the inner element has a non-uniform outer diameter.

21. The composite wire of claim 19, wherein at least one recess is formed in an outer surface of the inner element.

22. The composite wire of claim 19, wherein the inner element comprises a guide wire.

23. The composite wire of claim 19, wherein the second outer diameter defines a principal outer diameter of the composite wire.

24. The composite wire of claim 19, wherein the adhesive comprises a coupling element between the inner element and the outer element.

25. The composite wire of claim 24, wherein the adhesive comprises a UV-curable adhesive.

\* \* \* \* \*